United States Patent [19]

Kaster

[11] Patent Number: 4,532,659

[45] Date of Patent: Aug. 6, 1985

[54] PROSTHETIC HEART VALVE WITH PLANO-CONVEX DISK OCCLUDER

[75] Inventor: Robert L. Kaster, Plymouth, Minn.

[73] Assignee: Angicor Limited, Minneapolis, Minn.

[21] Appl. No.: 568,944

[22] Filed: Jan. 9, 1984

Related U.S. Application Data

[63] Continuation-in-part of Ser. No. 415,283, Sep. 7, 1982, abandoned.

[51] Int. Cl.$^3$ ................................................. A61F 1/22
[52] U.S. Cl. ..................................... 623/2; 137/527.8
[58] Field of Search ................... 3/1.5; 137/527.8, 527

[56] References Cited

U.S. PATENT DOCUMENTS 4,240,161 12/1980 Huffstutler, Jr. et al. ............... 3/1.5
4,343,049 9/1982 Fettel et al. ............................. 3/1.5

Primary Examiner—Richard J. Apley
Assistant Examiner—David Isabella
Attorney, Agent, or Firm—Henderson & Sturm

[57] ABSTRACT

In a prosthetic heart valve having a free floating, rotatable, pivotable disk occluder for blocking a flow of fluid therethrough, an improvement comprising the provision of a disk occluder (12) having a substantially convex distal surface (39) and a substantially planar proximal surface (38) having a concentrically disposed well (42) formed therein. A proximal positioned control unit (21) and a distal positioned control unit (22) are provided for cooperative interaction with the disk occluder (12) to support the disk occluder (12) in the occlude and non-occlude mode and to provide a pivot guide for transition between the occlude to non-occlude mode and for the transition between the non-occlude to the occlude mode.

15 Claims, 9 Drawing Figures

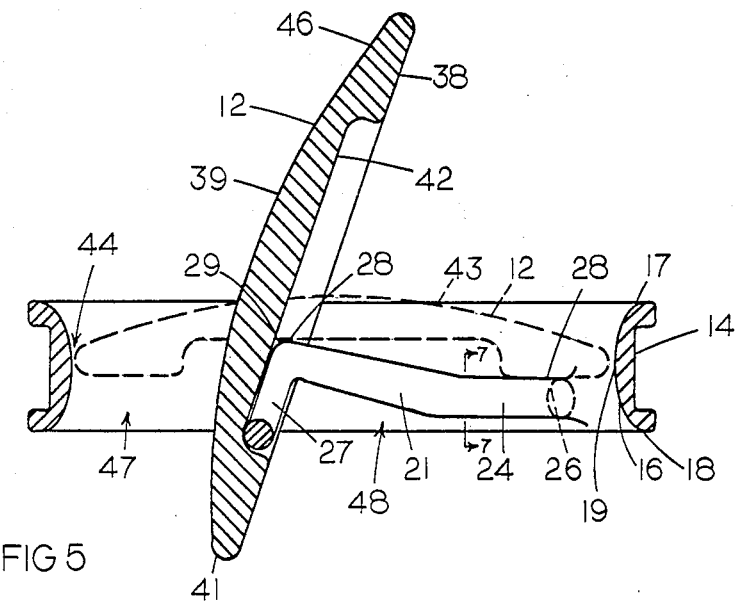
FIG 5
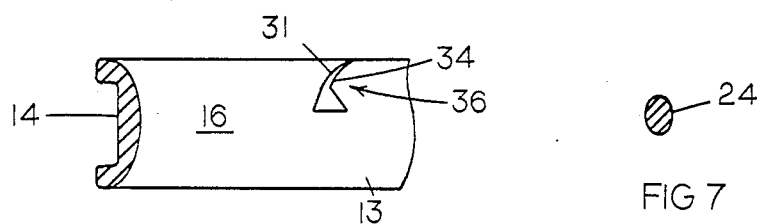
FIG 6
FIG 7
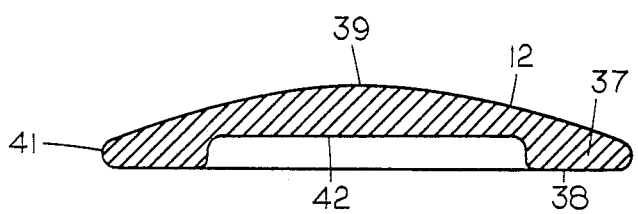
FIG 8

PROSTHETIC HEART VALVE WITH PLANO-CONVEX DISK OCCLUDER

This application is a continuation-in-part of application Ser. No. 415,283, filed Sept. 7, 1982 now abandoned.

TECHNICAL FIELD

This invention relates generally to artificial heart valves, and more particularly to heart valves that utilize a free-floating, rotatable, pivotable disk occluder.

BACKGROUND ART

The human heart serves as a four chambered double pump. For separate valves control the passage of blood between these chambers. When functioning properly, these natural valves operate as one way mechanisms that allow blood to flow in only one direction there through. When one of these valves operates defectively, serious health concerns arise. Often the defective valve must be replaced with a prosthetic device.

Artificial heart valves are utilized for the above purpose. Typically, such valves include a circular orifice and a flow regulating device such as a ball or disk that may be used to occlude the orifice passageway. Such implanted heart valves must withstand a number of stressful conditions and are otherwise subject to an unfavorable environment for artifacts. For instance, large static and dynamic inertias are evident as the heart pumps blood. Furthermore, a significant hemodynamic pressure gradient may be built up across the valve location. Heart valves are also subject to localized wear and breakdown, and can contribute to the creation of stagnation areas where clotting may occur.

Ideally, an artificial heart valve provides minimal opposition to the desired flow of blood and additionally encourages a centralized flow through the valve. Heart valves that make use of free floating, rotatable, pivotable disk occluders seem to meet these criteria best. Nevertheless, prior art devices that make use of such disk occluders still have not insignificant problems in accomodating the hemodynamic pressure gradient and in minimizing the creation of stagnation areas. Further, such disk occluders have not been as successful in encouraging a centralized flow of blood as might be otherwise desired.

DISCLOSURE OF INVENTION

The above problems are substantially resolved, without undue compromise of other desirable attributes noted above that are already provided by prior art devices, by provision of the invention disclosed herein. The invention includes generally a valve housing and a free floating, rotatable, pivotable disk occluder.

The disk occluder includes a substantially planar proximal surface and a substantially convex distal surface. (Throughout this specification and in the claims, the words "proximal" and "distal" are not used in their usual euclidean connotation. Rather, in cardiovascular practice, "proximal" refers to that place where blood enters a particular structure, and "distal" refers to that place where blood leaves a particular structure. Therefore, as used in reference to a disk occluder, "proximal" refers to that side of the disk occluder that normally faces the blood inflow port and the word "distal" refers to that side of the disk occluder that normally faces the blood outflow port.)

The substantially planar proximal surface of the disk occluder includes a well concentrically disposed therein that cooperates with a complimentary pivot and support structure that will be described further below. Finally, the disk occluder includes a rounded or curved periphery that smoothly joins the substantially convex distal surface with the substantially planar proximal surface.

The valve housing of the invention may be comprised generally of an annularly shaped base. This base includes a suture ring groove formed about the exterior periphery thereof for receiving a sewing ring to facilitate implantation of the valve within the heart. In addition, the inner circumference of the base may be rounded. The valve housing also includes a distal positioned control unit and a proximal positioned control unit.

The proximal positioned control unit may be comprised of a cantilevered structure that provides both an occlude mode support surface and a first non-occlude mode support surface that operates cooperatively with the well disposed on the disk occluder. (as used herein, a "support surface" includes a planar surface, line surface or point surface, without limitation.) The occlude mode support surface cooperates with both the well of the disk occluder and the planar surface thereof. In addition, the proximal positioned control unit provides a non-occlude to occlude mode transition pivot guide.

The proximal positioned control unit may be formed of a rod like structure that will sturdily support the pivot motion, occluding position and non-occluding position of the disk occluder while simultaneously presenting only a minimum barrier to the flow of blood.

The distal positioned control unit serves both as an occlude to non-occlude mode transition pivot guide and as a second non-occlude mode support surface. The distal positioned control unit may be provided by the use of two short projections that are located opposite one another along a cord of the valve housing. These projections are oriented substantially inwardly of the valve housing and cooperate with the convex surface of the disk occluder such that the disk occluder may pivot with respect to the projections and may further be supported thereby when in the non-occlude mode.

When blood pressure on the proximal side of the disk occluder exceeds the pressure on the distal side, the disk occluder will translate slightly distally and then pivot about the pivot guide surfaces of the distal positioned control unit. The disk occluder will come to rest against the support surfaces described above at approximately a 75° angle with the horizontal, and can move no further.

So positioned, two blood flow apertures are formed; one aperture being larger than the other. The larger aperture becomes formed between the valve housing and the proximal side of the disk occluder. The smaller aperture becomes formed between the valve housing and the distal side of the disk occluder.

The convex surface of the disk occluder cooperates with the planar surface of the disk occluder, when positioned in the non-occlude mode, to non-turbulently divide the flow of blood between the smaller and larger apertures. sufficient quantity of blood will pass non-turbulently through the smaller aperture such that the blood will be substantially centrally directed through the valve housing. The rounded edge of the disk occluder further enhances the non-turbulent passage of blood.

As a result, a heart valve utilizing this disk occluder well imitates the functioning of a natural heart valve with respect to the maintenance of a substantially centralized flow of blood.

BRIEF DESCRIPTION OF THE DRAWINGS

These and other attributes of the invention will become more clear upon a thorough study and review of the following detailed description of the best mode for carrying out the invention, particularly when reviewed in conjunction with the drawings, wherein:

FIG. 5 is a side elevational view of the invention sectioned along the line 5—5 as depicted in FIG. 3;

FIG. 6 is a detail sectioned side elevational view of the invention;

FIG. 7 is a sectioned detail view taken along the line 7—7 as depicted in FIG. 5;

FIG. 8 is a side elevational sectioned view of the disk occluder of the invention.

BEST MODE FOR CARRYING OUT THE INVENTION

Figure 1:
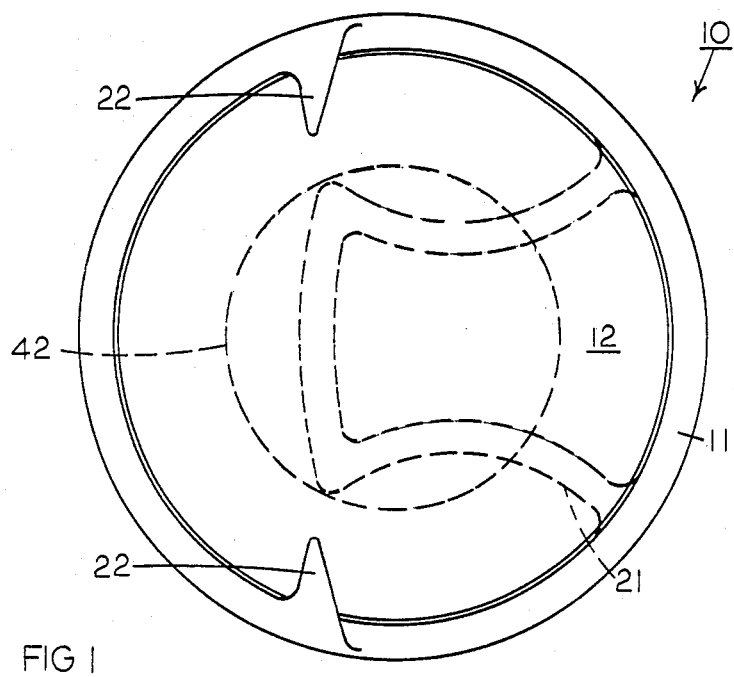
FIG. 1 is a top plan view of the heart valve with the disk occluder in the occlude mode.

Referring now to the drawings, and in particular to FIG. 1, the heart valve of the invention may be seen as depicted generally by the numeral 10. The heart valve (10) includes generally a valve housing (11) and a disk occluder (12). These general elements will now be described in seriatim fashion.

Figure 2:
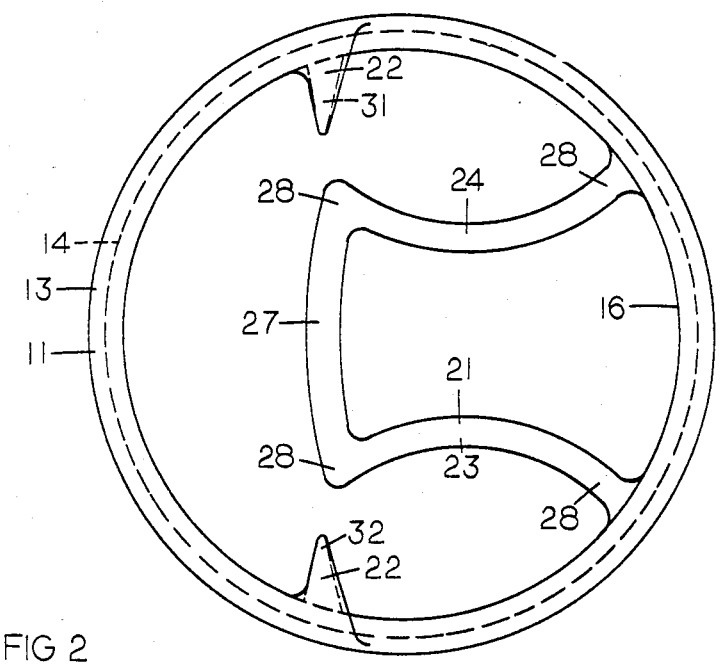
FIG. 2 is a top plan view of the heart valve with the disk occluder removed.
Figure 3:
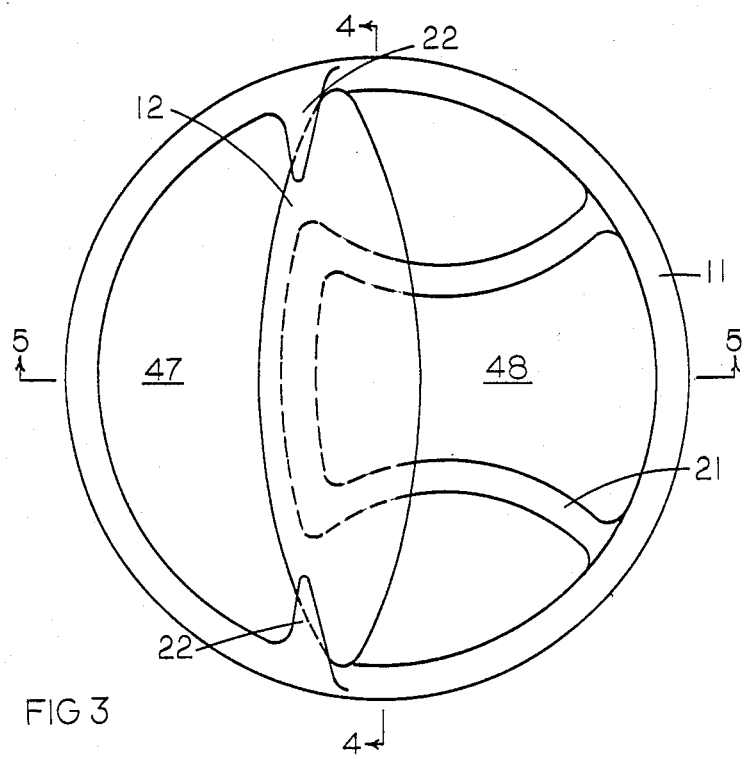
FIG. 3 is a top plan view of the heart valve with the disk occluder in the non-occlude mode.

Referring now to FIG. 2, the valve housing (11) will be described in detail. The valve housing (11) includes an annularly shaped base (13). This annularly shaped base (13) includes a suture ring groove (14) that is perhaps best depicted at FIG. 4. A sewing ring (not depicted) may be disposed within the suture ring groove (14) to facilitate implantation of the heart valve (10) within a heart (not shown). Such sewing rings are well known in the art. Therefore, no further detailed disclosure of such sewing rings need be made here.

With reference to FIG. 5, the interior circumferential surface (16) thereof may be crowned. More particularly, the interior surface (16) may widen in circumference at both edges (17 and 18) and be narrowest at the center (19). It may further be noted that the interior circumference at the edges (17 and 18) may be greater than the diameter of the suture ring groove (14). Such an arrangement will assist in assuring that the valve housing (11) obstructs the flow of blood therethrough as little as possible when implanted within a heart.

The valve housing (11) also includes an integrally formed distal positioned control unit (22) and a proximal positioned control unit (21). Both of these units (21 and 22) will now be described with reference to FIG. 2.

The proximal positioned control unit (21) attaches to the interior surface (16) of the valve housing (11). This connection may be accomplished through two curved rod like members (23 and 24) that are affixed to the proximal portion of the base (13) (see FIG. 5 at numeral 26). As represented in FIG. 7, both rod like members (23 and 24) have a generally elliptical cross section.

Both rod like members (23 and 24) are cantilevered towards the interior of the valve housing (11). Both rod like members (23 and 24) are then joined at their cantilevered ends by a generally U-shaped member (27), the U-shaped member (27) being perhaps best portrayed in FIG. 4.

A section of the distal surface of both ends of each rod like member (23 and 24) serves as an occlude mode support surface for the disk occluder (12). These areas of support are depicted generally by the numeral 28. Both cantilevered ends of the rod-like members (23 and 24) serve as a pivot guide for the disk occluder during the transition from the non-occluding mode to the occlude mode, these pivot guide areas being represented generally by the numeral 29.

The U-shaped member (27) serves as a non-occlude mode support surface as depicted in FIG. 5. A detailed description of cooperative functioning between the disk occluder and the proximal positioned control unit (21) will be provided below.

Preferably, the proximal positioned control unit (21) will be fashioned such that the valve housing base (13), the two rod like members (23 and 24) and the U-shaped member (27) will all be integrally formed.

The distal positioned control unit (22) may be comprised of two substantially triangularly shaped projections (31 and 32). Since each projection (31 and 32) constitutes a mirror image of the other, only one such projection (32) need be described in detail.

Figure 4:
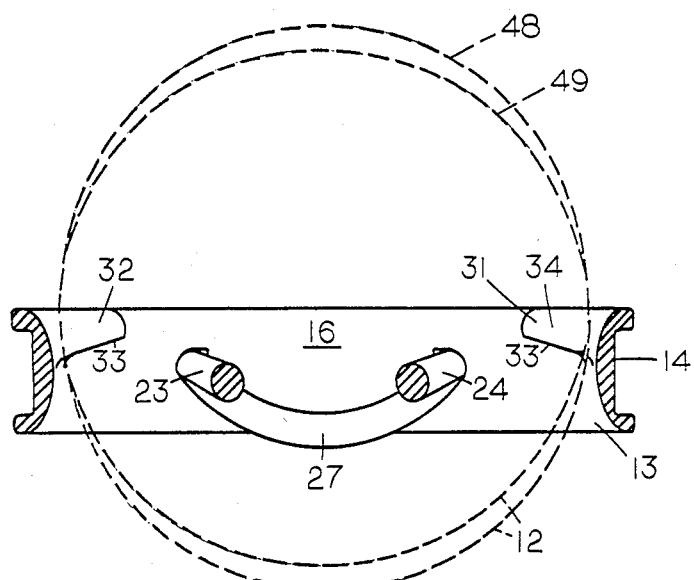
FIG. 4 is a front elevational view of the invention sectioned along the line 4—4 as depicted in FIG. 3.

The projection (32) attaches to the distal portion of the interior surface (16) of the base (13). As depicted in FIGS. 4 and 6, the underside surface (33) of the projection (31) angles upwardly somewhat from the horizontal plane. The inwardly disposed surface (34) of the projection (31) has a more arcuate shape. It may be seen that the inwardly disposed surface (34) curves to form a concave receiving area for operable cooperation with the convex surface of the disk occluder (12).

The distal positioned control unit (22) serves as a pivot guide for the disk occluder (12) during the transition from the occlude mode to the non-occlude mode. Second, the distal positioned control unit (22) serves as a support surface for the disk occluder (12) during the non-occlude mode. As with the proximal positioned control unit (21), the means of cooperation between the distal position control unit (22) and the disk occluder (12) will be described below.

Figure 9:
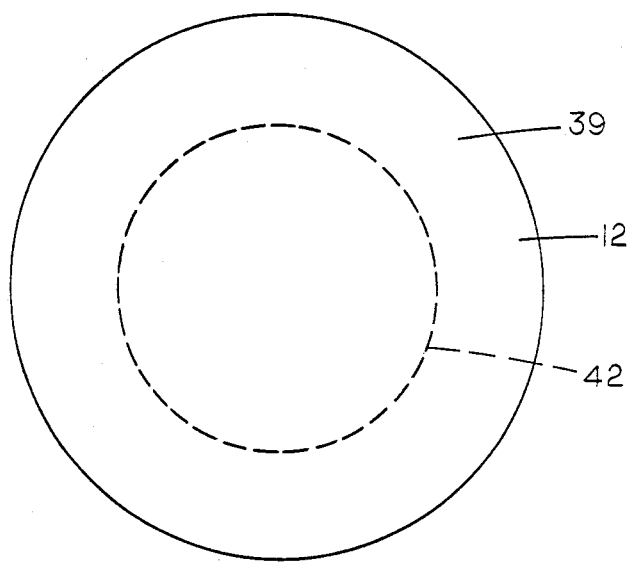
FIG. 9 is a top plan view of the disk occluder.

With reference to FIGS. 8 and 9, the disk occluder (12) comprises a substantially circular disk (37). This disk (37) has a substantially planar underside surface (38) and a substantially convex upper surface (39). The substantially planar under surface (38) will henceforth be referred to as the distal surface, and the substantially convex upper surface of the disk (37) will be referred to as the distal surface. The periphery of the disk (37) may be rounded (41) for reasons that are explained below. Finally, a well (42) may be concentrically disposed on the proximal surface of the disk (37) for cooperative interaction with the proximal positioned control unit (21). As viewed in FIG. 9, the well (42) comprises no more than approximately thirty-six percent of the area represented by the area bounded by the outer periphery of the disk (37).

Both the valve housing (11) and the disk occluder (12) should be formed of materials that are compatible with the host environment. In addition, the materials should preferably be radiopaque and be lightweight. Such materials could include Pyrolite-carbon, sapphire, ceramic, metals (such as titanium, tantalum, and stainless steel) and plastics (such as polypropylene, polycarbonate, polysulfone, polyethelene, Delrin, Teflon or the like). The applicant prefers the use of Pyrolite-carbon for the disk occluder and titanium for the valve housing (11).

The heart valve (10) may be constructed or formed by any known means that is coincidentally suitable for the material being used. Such means of manufacture include machining, casting, molding, welding, swagging, electron discharge machining (EDM), stamping or the like. For this particular heart valve, the applicant prefers a machining method.

Operation of the heart valve (10) will now be described. With reference to FIGS. 1 and 5, the disk occluder (12) may be seen in the occlude mode (in FIG. 5 the occlude mode is represented by phantom lines (43)). It will be appreciated that the base (13) does not include a circumferentially disposed seat or the like for interacting with the disk occluder (12). Rather, a small clearance on the order of 0.1 mm. (44) may be provided between the disk occluder periphery (41) and the crown (19) of the interior surface (16) of the valve housing base (13).

Rather than being supported by such a seat, the disk occluder (12) rests upon four different sections of the proximal positioned control unit (21). Such support has been provided near the base and terminus of the proximal positioned control unit (21) as represented by the numeral 28.

When in the occlude mode, the proximal positioned control unit (21) (FIG. 5) cooperatively interacts with the well (42) provided in the disk occluder (12). This cooperation assures that the disk occluder (12) may rotate about its axis as may be necessary, but the disk occluder will yet be prevented from unwanted lateral movement.

When blood pressure on the proximal side of the disk occluder increases and exceeds the blood pressure on the distal side of the disk occluder, the disk occluder (12) will begin the transition from the occlude mode (as depicted by the numeral 43) to the non-occlude mode (as depicted by the numeral 46). This transition begins with a small distal translation of the disk occluder (12) relative the valve housing (11). This translation may only continue until the distal surface (39) of the disk occluder (12) contacts the distal positioned control unit (22). Once such contact has been made, translation will substantially cease and pivoting will begin.

The disk occluder (12) will pivot about the projections (31 and 32) of the distal position control unit (22) until the disk occluder (12) contacts the non-occlude mode support surface (36) of the distal positioned control unit (22) and/or the non-occlude mode support surface represented by the U-shaped member (27) of the proximal positioned control unit (21). As such pivoting occurs, the disk occluder (12) will also be able to translate further in the distal direction, and such further translation does occur.

So disposed, the proximal surface (38) of the disk occluder (12) will be disposed at an angle of approximately 75° with respect to the horizontal. Other angular positions could be utilized as well, of course, within a range of approximately 50° to 89°.

It will be appreciated that when so positioned, the substantially planar distal surface (38), the rounded periphery (41) and the substantially convex distal surface (39) of the disk occluder (12) cooperate to divide and channel the blood flow as between two apertures that have been formed in the valve housing opening (11) by the position of the disk occluder (12) with minimum obstruction.

In this respect, it may be noted that the disk occluder (12) does not pivot about a centrally disposed axis. Rather, the pivoting occurs off center. Therefore, the aperture formed between the valve housing (11) and the distal portion of the disk occluder (12) constitutes a smaller aperture (47) than the aperture (48) formed between the valve housing (11) and the proximal side (38) of the disk occluder (12).

The shape and position of the disk occluder (12) assures that blood will be directed through both the smaller and larger apertures (47 and 48) to promote a substantially centralized flow of blood through the valve housing (11).

When pressure on the distal side of the valve housing (11) begins to exceed that on the proximal side, the disk occluder (12) will begin the transition from the non-occlude mode (46) to the occlude mode (43). This transition begins with a small proximal translation of the disk occluder (12). This translation has been depicted by the use of phantom lines in FIG. 4, wherein the numeral 48 refers to the distal position of the disk occluder (12) and the numeral 49 refers to the proximal position thereof.

The disk occluder (12) continues this translation to the proximal position (49) until the periphery of the disk occluder (41) contacts the interior surface (16) of the base (13). When such contact has been made, the disk occluder will pivot about the pivot surface represented by the numeral 29 on the proximal positioned control unit (21). Such pivoting will continue until the disk occluder (12) assumes the complete occlude mode position (43).

It will be appreciated that the heart valve (10) of the invention achieves all of the benefits of earlier free floating, rotatable, pivotable disk occluder heart valves, and that the heart valve (10) of the invention achieves further advantages as well. Most importantly, this heart valve (10) assures a more centralized and non-turbulent flow of blood through the heart valve (10) with all of its attendant advantages.

Other advantages are obtained as well. For instance, the proximal positioned control unit (21) cooperates with the inner surface of the concentrically disposed well (42) to aid in preventing the disk (37) from moving further in the distal direction when in the non-occlude position. Also, disk (37) can freely rotate about the proximal positioned control unit (21). As a result, biologic deposits such as coagulated blood can be continually washed from the proximal surface of the disk (37), including the concentrically disposed well (42), by interaction between these two parts.

Obviously, many modifications and variations of the present invention are possible in light of the above teachings. It is therefore to be understood that, within the scope of the appended claims, the invention may be practised otherwise than as specifically described.

I claim:

1. In a prosthetic heart valve of a type having a valve housing adapted to be attached to a blood carrying vessel; a passageway disposed through said housing for permitting blood to flow therethrough, said passageway having a proximal inlet side and a distal outlet side; disk occluder means disposed within said passageway in the valve housing for permitting the flow of blood from the proximal inlet side of the passageway to the distal outlet side of the passageway and for substantially preventing the flow of blood from the distal outlet side to the proximal inlet side of the passageway, said disk occluder means including a disk disposed within said passageway, said disk having an outer peripheral edge, a proximal side and a distal side; means for causing said disk to be free floating and rotatably disposed within said passageway for preventing wear thereof, and means associated with said housing for causing said disk to be pivotable within said passageway between a closed position wherein the outer peripheral edge is in close proximity to the passageway and an open position wherein a substantial portion of said peripheral edge is spaced from said passageway to permit flow through said passageway; the improvement comprising:

(a) a substantially planar surface on the proximal inlet side of said disk, said planar surface being located radially inwardly from said outer peripheral edge; and (b) a concentrically disposed well formed in said planar surface, the area of said well comprising no more than approximately thirty-six percent of the total area of said proximal side of said disk whereby the position of the disk can be controlled.

2. The improvement of claim 1 wherein said disk further includes a substantially convex distal surface.

3. The improvement of claim 1 wherein said heart valve further includes a proximal positioned control means and a distal positioned control means for operable interaction with said disc, such that said disk may be at least partially supported by said proximal positioned control means when in an occlude closed position and at least partially supported by said distal positioned control means when in a non-occlude open position.

4. The improvement of claim 1 wherein at least part of said concentrically disposed well contacts at least part of said proximal positioned control means during at least part of the movement of said disk between the non-occlude open position to the occlude closed position.

5. The improvement of claim 1 wherein at least part of said substantially convex distal surface of said disk contacts at least part of said distal positioned control means during at least part of the movement of the disk between the occlude closed position to the non-occlude open position.

6. The improvement of claim 1 wherein said disk is also at least partially supported by said proximal positioned control means when in a non-occlude open position.

7. The improvement of claim 1 wherein said proximal positioned control means cooperates with said concentrically disposed well when said disk is in a fully non-occlude open position to prevent said disk from moving further in a distal direction.

8. The improvement of claim 1 wherein said proximal positioned control means cooperates with said concentrically disposed well to aid in the prevention of the accumulation of unwanted biologic material within said concentrically disposed well.

9. The improvement of claim 1 wherein:

(a) said valve housing comprised of a substantially annularly shaped base having a suture ring groove formed thereabout and a substantially rounded inner circumference, such that said proximal and distal positioned control means are affixed to said valve housing and extend inwardly thereof; and (b) said proximal positioned control means comprises first and second rod members, each said rod member having a first end affixed to said valve housing and a second end cantilevered inwardly of said valve housing.

10. The improvement of claim 9 wherein a substantially U-shaped member affixes to the second end of both of said first and second rod members.

11. The improvement of claim 10 wherein said distal positioned control means comprises first and second substantially triangularly shaped projections, each said projection extending inwardly of said valve housing and each having a receiving surface for operable cooperation with the distal surface of said disk.

12. In a prosthetic heart valve of a type having a valve housing adapted to be attached to a blood carrying vessel; a passageway disposed through said housing for permitting blood to flow therethrough, said passageway having a proximal inlet side and a distal outlet side; disk occluder means disposed within said passageway in the valve housing for permitting the flow of blood from the proximal inlet side of the passageway to the distal outlet side of the passageway and for substantially preventing the flow of blood from the distal outlet side to the proximal inlet side of the passageway, said disk occluder means including a disk disposed within said passageway, said disk having an outer peripheral edge, a proximal side and a distal side; means for causing said disk to be free floating and rotatably disposed within said passageway for preventing wear thereof, and means associated with said housing for causing said disk to be pivotable within said passageway between a closed position wherein the outer peripheral edge is in close proximity to the passageway and an open position wherein a substantial portion of said peripheral edge is spaced from said passageway to permit flow through said passageway; the improvement comprising:

(a) a substantially planar surface on the proximal inlet side of said disk, said planar surface being located radially inwardly from said outer peripheral edge;

(b) a concentrically disposed well formed in said planar surface; and (c) a proximal positioned control means attached to said valve housing for contact and operable interation with said disk occluder well during at least part of the movement between the non-occlude open position and the occlude closed position whereby said proximal positioned control means is controlled by the proximal positioned control means in its movement between the non-occlude open position and the occlude closed position.

13. The improvement of claim 12 wherein:

(a) said valve housing is comprised of a substantially annularly shaped base having a suture ring groove formed thereabout and a substantially rounded inner circumference, such that said proximal and distal positioned control means are affixed to said valve housing and extend inwardly thereof; and (b) said proximal positioned control means comprises first and second rod members, each said rod member having a first end affixed to said valve housing and a second end cantilevered inwardly of said valve housing.

14. The improvement of claim 13 wherein a substantially U-shaped member affixes to the second end of both of said first and second rod members.

15. The improvement of claim 14 wherein said distal positioned control means comprises first and second substantially triangularly shaped projections, each said projection extending inwardly of said valve housing and each having a receiving surface for operable cooperation with the distal surface of said disk.

* * * * *